United States Patent [19]

Mugica

[11] Patent Number: 5,428,013
[45] Date of Patent: Jun. 27, 1995

[54] DIFFERENTIAL DIAGNOSIS AND TREATMENT OF THE STATES OF GROWTH HORMONE INSUFFICIENCY (OR DEFICIENCY) WITH AN ALPHA-2-ADRENERGIC AGONIST AND A GROWTH HORMONE RELEASING PEPTIDE

[76] Inventor: Jesus D. Mugica, Chalet "As Gaivotas," Lamas Cacheira, 15883 Teo (La Cornua), Spain

[21] Appl. No.: 947,277

[22] Filed: Sep. 18, 1992

Related U.S. Application Data

[63] Continuation of Ser. No. 637,362, Jan. 4, 1991, abandoned.

[51] Int. Cl.$^6$ .................. A61K 31/415; A61K 38/25; A61K 38/27; A61K 49/00
[52] U.S. Cl. .......................................... 514/12; 514/2; 514/401; 436/518; 436/542; 436/536
[58] Field of Search .................. 424/9; 514/2, 12, 401

[56] References Cited

U.S. PATENT DOCUMENTS

| | | | |
|---|---|---|---|
| 4,747,825 | 5/1988 | Linkie et al. | 514/12 |
| 5,065,747 | 11/1991 | Bercu | 424/9 |
| 5,120,713 | 6/1992 | Mugica | 514/12 |

OTHER PUBLICATIONS

Van Vliet et al, "Growth Hormone Treatment . . . ", *New Eng J. Med.* 309: 1016–1022, (1983).
Reiter et al, "Modulation of GHRH-Induced . . . ", *J. Ped. Endocrin.* 3(1): 21–25 (1988).
Gil-Ad et al, "Oral clonidine as a growth hormone stimulation test", *The Lancet* 2:278–280 (1979).
Devesa et al, "$\alpha_2$-adrenergic agonism enhances the growth hormones . . . " *J. Clin. Endo. & Metab.* 71(6):1581–1588 (1990).

*Primary Examiner*—Stephen G. Walsh

[57] ABSTRACT

Differential diagnosis of diverse GH-deficient states may be effectively established by cojointly administering an alpha-2-adrenergic agonist, such as clonidine, and a growth hormone releasing peptide such as GHRH. In addition, some children with short stature and showing a positive response to this test may effectively be treated with such administration.

19 Claims, No Drawings

DIFFERENTIAL DIAGNOSIS AND TREATMENT OF THE STATES OF GROWTH HORMONE INSUFFICIENCY (OR DEFICIENCY) WITH AN ALPHA-2-ADRENERGIC AGONIST AND A GROWTH HORMONE RELEASING PEPTIDE

This is a continuation of application Ser. No. 07/637,362 filed Jan. 4, 1991, now abandoned.

FIELD OF THE INVENTION

The present invention relates to the differential diagnosis of the various states of growth hormone insufficiency or deficiency. The invention also relates, in those cases in which a positive response could be expected, to the treatment with an alpha-2-adrenergic agonist and a growth hormone-releasing peptide to induce growth hormone secretion in children, particularly those children growing between the tenth ($P_{10}$) and third ($P_3$) percentile, and most particularly children with stature below the third percentile ($P_3$).

BACKGROUND OF THE INVENTION

From a clinical point of view, it is clear that it would be helpful to use a biochemical test to better understand and differentiate the various states of growth hormone (GH) deficiency. The availability of such a test would permit the identification of the defect leading to the GH insufficiency and its degree; as well as to better decide when a GH treatment is needed and when it must be started. All conventional dynamic tests (i.e. clonidine, levodopa, arginine, insulin hypoglycemia) (Gil-Ad, *Lancet* 2:278, 1979; Plotnik, *J. Clin. Endocrinol. Metab.*, 48:811, 1979; Frasier, *Pediatrics*, 53:929, 1974; Underwood, "Normal and Aberrant Growth," *Williams Textbook of Endocrinology* (eds. Wilson and Foster) p. 155, 1985, Saunders, Philadelphia) are unable to differentiate between GH-deficiency due to pituitary defect and that due to hypothalamic dysfunction involving the mechanisms engaged in GH neuroregulation. Moreover, these tests do not distinguish between hypothalamic defects leading to transiently or chronically impaired GH secretion; or particularly between Constitutional Growth Delay and Familial Short Stature, especially when, as is frequently observed, the former condition coexists with the genetic cause.

It was expected that the availability of growth hormone-releasing hormone (GHRH) would improve the ability to define GH-deficient states; however, the majority of growth hormone deficient subjects have a hypothalamic dysfunction and the majority of subjects tested have GH secretion in response to GHRH regardless of the etiology of their GH deficiency (Chatelain, *Pediatric Research*, 19:610, 1985). Otherwise, non-responder subjects could have been tested in a refractory hypothalamic somatotroph rhythm (HSR) phase (Devesa, *Clinical Endocrinology* (Oxf), 30:367, 1989), occurring either physiologically, during a normal trough period, or pathologically, as a consequence of a chronically increased somatostatinergic tone. Therefore, the use of GHRH alone has now been discarded for that purpose.

It is known that administering an agent to a normal subject that interferes with the hypothalamic release of somatostatin will enhance growth hormone release. This effect has been shown for clonidine, an alpha-2-adrenergic agonist, and pyridostigmine, a cholinergic agonist, although the mechanism of action is different for each drug (Ghigo, *J. Endocrinol. Invest.*, 12:99, 1989). Likewise, galanin has been shown to potentiate GHRH-induced GH secretion in normal subjects (Davis, *J. Clin. Endocrinol. Metab.*, 65:1248, 1987) via the cholinergic pathways (Chatterjee, *J. Endocrinol.*, 116:R1-R2, 1988). It has also been recently postulated that the pyridostigmine plus GHRH test would allow the differentiation of GH deficiency due to pituitary secretory inability from that due to a hypothalamic defect, without distinguishing between the different states of GH neurosecretory dysfunctions (i.e., Congenital Delay of Growth, GH Neurosecretory Dysfunction) and Familial Short Stature (Ghigo, "Effects of the Enhancement of the Cholinergic Activity on Growth Hormone Secretion in Children: Clinical Implications," *Recent Advances in Basic and Clinical Neuroendocrinology* (eds. Casanueva and Dieguez), pp. 241-250, 1989, Excerpta Medica, Amsterdam). However, the fact that alpha-2-adrenoceptor blockade blunted the enhanced GH response to pyridostigmine plus GHRH (Devesa, [Devesa Mugica, the inventor herein] *Abstracts Book*, XII Panamerican Congress of Endocrinology, held November 2-8, 1990, Recife, Brazil) indicates that false negative responses (i.e. false pituitary defects) may also occur when utilizing this test. Moreover, pyridostigmine does not represent a useful treatment of short stature (Ghigo, "Effects of the Enhancement of the Cholinergic Activity on Growth Hormone Secretion in Children: Clinical Implications," *Recent Advances in Basic and Clinical Neuroendocrinlogy* (eds. Casanueva and Dieguez), pp. 241-250, 1989, Excerpta Medica, Amsterdam). While it has been shown that pretreatment with clonidine enhances the GH response to GHRH in short, normal children and adults (Reiter, *J. Pediatr. Endocrinol.*, 3:21, 1988; Devesa [Devesa Mugica, the inventor herein] et al. *J. Clin. Endocrinol. Metab.*, 71:1581-1588, 1990, it was not known whether such treatment could be extended to the differential diagnosis and treatment of the various states of GH-insufficiency in children.

SUMMARY OF THE INVENTION

It has now been discovered that the various GH-deficient states may be effectively differentiated by cojointly administering an alpha-2-adrenergic agonist, such as clonidine, and a growth hormone releasing peptide, such as GHRH. This test both explores the functionality of the main hypothalamic structures involved in GH control, and directly assesses the secretory integrity of somatotropes. Therefore, no false negative responses are expected to occur. Moreover, it minimizes, at high GH levels, the variability in GH responses to GHRH, thus allowing its use in the treatment of short children having a hypothalamic dysfunction responsible for their diminished linear growth.

DETAILED DESCRIPTION OF THE INVENTION

Until now, all of the known provocative tests for GH secretion were unable to characterize the various GH-deficient states, and the unique effective treatment for hypothalamic GH deficiency was the administration of exogenous GH. A unique and effective test for differential diagnosis and treatment of such patients has now been found. This test involves administering cojointly to children of short stature an effective amount of an alpha-2-adrenergic agonist and a growth hormone releasing peptide.

The alpha-2-adrenergic agonist may be any of those which produce a post-synaptic stimulation of the alpha-2-adrenergic agonist pathway so as to inhibit somatostatin release by the hypothalamus into the hypothalamic pituitary portal system. Alpha-2-adrenergic agonists which may be utilized include clonidine (2-(2,6-dichloroanilino)-2-imidazoline), guanfacine, guanabenz, guanclofine, guanoxabenz (U.S. Pat. No. 4,910,215) and medatomidine (U.S. Pat. No. 4,910,214). Clonidine is preferred. The dosage is adjusted in accordance with the needs of the patient and the result desired. Typically, clonidine is administered orally at a dosage of about 100 to about 300 ug/m$^2$, preferably about 150 ug/m$^2$. It is preferably administered from 0 to about 120 minutes, most preferably about 60 minutes, prior to administering the growth hormone releasing peptide.

The growth hormone releasing peptide which may be utilized includes those peptides which stimulate a GH response at the GHRH level, i.e. stimulate the pituitary somatotropes. Such peptides include GHRH itself in its various known active forms such as growth hormone-release factors (GRF) GRF 1-44, GRF 1-40, GRF 1-37 and GRF 1-29. GHRH is typically administered by injection intravenously (i.v) or subcutaneously (s.c.), and may be advantageously delivered in a pulsatile manner (e.g. by infusion pump) or continuously (e.g. long-term preparations). The dosage is typically about 1 ug/kg if administered by i.v. bolus, or about 10 ug/kg s.c., for acute tests, or about 3 ug/kg/h for chronic treatment. Obviously, the dosage can be adjusted to meet the needs of the particular patient under diagnosis or treatment and the desired objective.

Other growth hormone-releasing peptides which can be effectively utilized are those short chain peptides (4–11 amino acids, preferably 5–7 amino acids) which have been recently found to stimulate a GH response similar to GHRH. These peptides include, but are not limited to those active peptides which are disclosed in U.S. Pat. No. 4,223,019, U.S. Pat. No. 4,223,020, U.S. Pat. No. 4,223,021, U.S. Pat. No. 4,224,316, U.S. Pat. No. 4,226,857, U.S. Pat. No. 4,228,155, U.S. Pat. No. 4,228,156, U.S. Pat. No. 4,228,157, U.S. Pat. No. 4,228,158, U.S. Pat. No. 4,410,512, U.S. Pat. No. 4,410,513, U.S. Pat. No. 4,411,890, U.S. Pat. No. 4,839,344, U.S. Pat. No. 4,880,777, U.S. Pat. No. 4,880,778, WO 89/07110, WO 89/07111 and WO 89/10933. Of the peptides disclosed in the above-identified patents, especially preferred are peptides of the formula:

$AA_1$-His-$AA_3$-Ala-TrP-D-Phe-Lys-$NH_2$ wherein $AA_1$ is H or Ala and $AA_3$ is preferably D-Trp, as well as analogs and derivatives thereof with similar activity.

EXAMPLE

Twenty-four children (17 boys and 7 girls) with stature below the third percentile ($P_3$), participated in the study with informed consent (parent and child). Ages of the children ranged from 7 to 13.9 years. In all but seven of the children, weight was more than or equal to $P_3$. Three of these children showed evidence of malnourishment. Two children had received prophylactic cranial irradiation due to brain tumors, five and three years before the study. Three children had been treated with GH for 9 months; their growth velocity increased during this therapy from 3 to 8 cm/yr. All children had been previously studied for their GH insufficiency. Studies included growth velocity, bone age, classical provocative tests for GH secretion (i.e. clonidine, insulin hypoglycemia and propranolol plus exercise), plasma somatomedin C (Sm C) (Insulin Growth Factor-I (IGF-I)) analysis, and analysis of the spontaneous pattern of nocturnal GH secretion. On the basis of a low GH response ($<10$ μg/L) to provocative tests, 50% of the children appeared to have a GH-deficiency after challenge with clonidine; this also occurred in 42% of the cases when tested with propranolol plus exercise, and in five of the six cases in which an insulinic hypoglycemia was achieved. Despite these results, in all but six children, indices of total and pulsatile nocturnal GH release appeared to be normal; plasma Sm C values were below normal limited for age in 18 of them. Mean ($\pm$SEM) plasma Sm C was $488\pm376$ U/L. Mean ($\pm$SEM) growth velocity was $3.7\pm0.9$ cm/yr.

For comparison purposes, twenty age-matched normal children (14 boys and 6 girls) were studied. Studies in this group included evaluation of growth velocity and bone age at the time of performing the combined test with clonidine plus GHRH.

Studies commenced at 09.00 h after an overnight fast and bed rest and thirty minutes after the insertion of a nonthrombogenic catheter for blood withdrawal in a forearm vein. The study consisted of administering clonidine (Catapresan, Boehringer Ingelheim, Spain) orally at 150 micrograms/m$^2$ at time 0, followed by administering GHRH (GRF 1-29, Serono, Spain) as an intravenous bolus at 1 microgram/kg at time 60 minutes. An additional control for short children consisted of administering a placebo at time 0, followed by administering GHRH at time 60 minutes. Blood samples for GH analysis (RIA, BioMérieux, France) were taken at 0 and 60 minutes and at 15 minute intervals for one hour following GHRH administration. The mean intra-assay coefficient of variation was 5.7, 3.2 and 4.3% at mean GH concentrations of 1.5, 10 and 22 micrograms/L respectively. To avoid interassay variations, all samples from a subject were run in the same assay.

Pretreatment with clonidine led to a clear GH response to GHRH in normal children, with a peak value of $41.6\pm3.5$ μg/L. A multiple regression analysis showed that there was a significant positive correlation between the amplitude of GH response and both chronological and bone age ($R=0.832$; $F=37.6$; $p=0.001$; $y=a+b\times BA+c\times CA$, where y=GH peak, BA=bone age, CA=chronological age). This was also observed between GH peaks and the bone age/growth velocity ratio in this group of normal children.

Baseline plasma GH levels in short children were not different during the 2 study days. GHRH-induced GH response after pretreatment with placebo was deficient in 9 patients (GH peak $<10$ μg/L), but no relationship was observed between this low response to GHRH and low responses in the other provocative tests, plasma Sm C, bone age or growth velocity. Pretreatment with clonidine led to a significantly higher GH response to GHRH in all but four children, but the range of these positive responses oscillated between 23.5 and 80.7 μg/L. A multivariate regression analysis established the existence of a close relationship ($R=0.71$; $p=0.01$) between the amplitude of clonidine plus GHRH elicited GH peaks and growth velocity, bone age and plasma Sm C levels, in those children in which a positive GH response to this test was found. Partial F table for this analysis showed that the strongest probability corresponded to growth velocity ($F=8.92$; $p=0.009$).

To confirm the uniqueness of such combined clonidine plus GHRH test in the differentiation of GH-deficient states, the theoretical GH responses to this test in short children were calculated on the basis of the equation obtained from the multiple regression analysis relating chronological and bone age with the amplitude of GH peaks in normal children. The percentage of deviation between theoretical values thus obtained and real values after the clonidine plus GHRH test ranged between −435 and +41%. Responses between the −20 to +20% range were considered to be normals, as they fitted between the standard deviation from the mean in the group of normal children. Plotting those responses against the standard deviation of the bone age to growth velocity ratio, five well defined populations were showed to exist: 1) Low responders with low growth velocity for bone age; 2) Low responders with normal growth velocity for bone age; 3) Normal responders with low growth velocity for bone age; 4) Normal responders with normal growth velocity for bone age; and 5) High responders with low growth velocity for bone age.

The results of these experiments are summarized in the following Table I, Table II and Table III:

TABLE I

| Patient Group (Number of Short Children) | % DT-R | GY | Sm C | MCGH | CA | BA |
|---|---|---|---|---|---|---|
| 1(6) | −211 ± 163 | 2.8 ± 0.06 | 318 ± 62 | 4.1 ± 2.1 | 10.9 ± 2.1 | 8.3 ± 2 |
| 2(5) | −69 ± 36 | 4.5 ± 0.4 | 394 ± 13 | 5.2 ± 0.9 | 11 ± 1.3 | 8.1 ± 1.7 |
| 3(5) | 9 ± 6.2 | 3.6 ± 0.4 | 434 ± 73 | 4.9 ± 2 | 8.4 ± 1.2 | 5.9 ± 1.7 |
| 4(5) | 4 ± 9 | 4.4 ± 1 | 976 ± 345 | 5.9 ± 1 | 11 ± 2.2 | 8.4 ± 3 |
| 5(3) | 36 ± 5 | 3.3 ± 0.3 | 263 ± 55 | 7.8 ± 1.8 | 8.3 ± 1.2 | 4.6 ± 1.5 |

% DT-R = Deviation between theoretically calculated and real GH peak response to clonidine plus GHRH. GY = Growth velocity (cm/yr.). Sm C (U/L).
MCGH = mean plasma GH concentration (µg/L) during a nocturnal period sampling. CA, BA = Chronological and bone age (years), respectively.
Values are the mean ± SE.

TABLE II

| Group | Mean GH peak response to GHRH | Mean GH peak response to clonidine plus GHRH |
|---|---|---|
| Normal children | — | 41.6 ± 3.5 (µg/L) |
| Short children | 19.5 ± 15.7 | 42.2 ± 19 |

TABLE III

Number of positive (+, >10 µg/L) or negative (−, <10 µg/L) GH responses to the different provocative tests.

| Patient Group (Short Children) | P + E | Clo | IH | GHRH | Clo + GHRH |
|---|---|---|---|---|---|
| 1 | +3,−3 | +0,−6 | −6 | +2,−4 | +4,−2 |
| 2 | +3,−2 | +4,−1 | — | +3,−2 | +5 |
| 3 | +3,−1 | +2,−2 | — | +3,−1 | +4 |
| 4 | +4,−1 | +3,−2 | — | +3,−2 | +5 |
| 5 | +1,−1 | +1,−2 | +1 | +3 | +3[1] |

[1]Two children in this group did not increase GH peak after clonidine plus GHRH as compared to that observed after GHRH alone. P + E = propranolol plus exercise. Clo = clonidine. IH = insulinic hypoglycemia.

This data is evidence of the uniqueness of the clonidine plus GHRH test to allow better differentiation among the diverse GH-deficient states, and therefore optimize the decision about which children must be treated and when the treatment must start. While classical GH tests in this and other studies, including pyridostigmine plus GHRH (Ghigo, "Effects of the Enhancement of the Cholinergic Activity on Growth Hormone Secretion in Children: Clinical Implications," *Recent Advances in Basic and Clinical Neuroendocrinology* (eds. Casanueva and Dieguez), pp. 241–250, 1989, Excerpta Medica, Amsterdam), do not differentiate between pituitary or hypothalamic defect, or among theoretically different hypothalamic dysfunction, the combined administration of clonidine and GHRH allowed these categorizations to be made well beyond any provocative test previously studied.

According to the results of this test, children from Group 1 are GH-deficients, from pituitary origin in two of them, and hypothalamic (neurosecretory dysfunction) in the other four. While the first two need to be treated with GH, the other four would benefit from a clonidine and GHRH treatment. Group 2 is composed of children with Constitutional Growth Delay; therefore no GH therapy is needed in this group, while a clonidine plus GHRH treatment would improve growth velocity in these children. Group 3 and Group 4 were composed of children having Familial Short Stature with or without Constitutional Growth Delay. The main difference between the two groups was due to the beginning of puberty in most of the children of Group 4, while all of the children in Group 3 were prepubertal. A more complete analysis of these children revealed the existence of differences in the GH response to clonidine plus GHRH between those cases in which Familial Short Stature was associated with Constitutional Growth Delay and those cases in which sexual maturation was normal. Children from Group 5 were malnourished, hence pretreatment with clonidine did not significantly enhance the GH response to GHRH.

In summary, the combined test with clonidine and GHRH allows the differentiation among diverse GH-deficient states. This single test places the subjects in a similar basal state thus eliminating interferences due to the hypothalamic-somatotroph rhythm (Devesa, [Devesa Mugrcal] *Clinical Endocrinology* (Oxf), 30:367, 1989). GH responses would therefore be a real expression of the pituitary reserve in hormone, indicating the functionality of the hypothalamus-somatotrope axis. Hence, this test does not give false negative responses and facilitates the differential diagnosis of GH-deficiency without the need for other provocative tests or the analysis of spontaneous GH secretion. Also, some children growing below the third percentile and showing a positive response to this test, independently of the degree of deviation from theoretically calculated values, would benefit from such a treatment. The superior effect of the pretreatment with alpha-2-adrenergic agonists such as clonidine is believed to result from the direct inhibition of somatostatin, unlike the indirect inhibition that occurs with the cholinergic agonists.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Method of providing for differential diagnosis of one of the various states of growth hormone insufficiency in a child of growth stature below the tenth percentile, which comprises in a standardizing procedure, cojointly administering an alpha-2-adrenergic agonist in an amount effective to inhibit somatostatin release by the hypothalamus and a growth hormone releasing peptide in an amount effective to stimulate growth hormone release, to a plurality of first children of normal growth stature, not exhibiting growth hormone insufficiency, and of known chronological ages, bone ages and growth velocities, said peptide stimulating a growth hormone response consequent said administering of said agonist, ascertaining by assay the elicited amounts of growth hormone release, and correlating the ascertained elicited amounts with the known chronological ages, bone ages and growth velocities of the first children to obtain a set of standard responder data including mean and standard deviation values of the growth hormone release elicited amounts and of the corresponding bone age to growth velocity ratios, for indicating the theoretical growth hormone release elicited amount corresponding to a child of known chronological age, bone age and growth velocity, in a test procedure, cojointly administering said agonist and peptide in said amounts, to a plurality of second children of growth stature below the tenth percentile, individually exhibiting respectively one of the various states of growth hormone insufficiency, and of known chronological ages, bone ages and growth velocities, ascertaining by assay the elicited amounts of growth hormone release and thereby individually those above a predetermined amount constituting about 10 micrograms/L for defining a positive response and those below said predetermined amount for defining a negative response, and correlating the ascertained elicited amounts with the known chronological ages, bone ages and growth velocities of the second children to obtain a set of test responder data, and in a diagnosing procedure, correlating said test data with said standard data, including correlating the test procedure growth hormone release elicited amounts with the standardizing procedure theoretical growth hormone release elicited amounts corresponding to the chronological ages, bone ages and growth velocities of the second children to provide a percentage deviation of the test procedure elicited amounts relative to the theoretical elicited amounts for defining a normal response as being within an about $-20$ to $+20\%$ deviation range and within the standard deviation value of the standard responder data growth hormone release elicited amounts, a low response as being below said deviation range and a high response as being above said deviation range, and correlating the percentage deviation defined responses with the standard deviation values of the corresponding bone age to growth velocity ratios of the standard responder data, to form a corresponding chronological age, bone age and growth velocity based data system for differentially diagnosing the second children among the following groups of growth hormone responders to said test procedure:

(1) a low responder having low growth velocity for corresponding bone age, such that the responder having said positive response is diagnosed as having neurosecretory dysfunction and the responder having said negative response is diagnosed as having pituitary dysfunction, (2) a low responder having normal growth velocity for corresponding bone age is diagnosed as having constitutional growth delay, (3) a normal responder having low growth velocity for corresponding bone age is diagnosed as having pre-pubertal familial short stature, (4) a normal responder having normal growth velocity for corresponding bone age is diagnosed as having post-pubertal familial short stature, and (5) a high responder having low growth velocity for corresponding bone age is diagnosed as malnourished, wherein a normal responder is defined as having a said growth hormone release within said about $-20$ to $+20\%$ deviation range, a low responder is defined as having a said growth hormone release lower than that of a normal responder, and a high responder is defined as having a said growth hormone release higher than that of a normal responder, and on the basis of said data system, for differentially diagnosing a child of growth stature below the tenth percentile and of known chronological age, bone age and growth velocity, and suspected of having a growth hormone deficiency, cojointly administering to the child said agonist and peptide in said amounts, and ascertaining by assay the elicited amount of growth hormone release and thereby whether the elicited amount is above said predetermined amount for defining a positive response or below said predetermined amount for defining a negative response, whereby to indicate on the basis of the ascertained elicited amount and said positive or negative response and the known chronological age, bone age and growth velocity of the child, by way of differential diagnosis, whether the child corresponds to one of the aforesaid groups (1) to (5) of growth hormone responders to such cojoint administration.

2. Method of claim 1 wherein said growth stature below the tenth percentile is below the third percentile.

3. Method of claim 1 wherein said agonist is clonidine.

4. Method of claim 3 wherein said clonidine is administered from 0 to about 120 minutes prior to said peptide.

5. Method of claim 3 wherein said clonidine is administered in an amount of from about 100 to about 300 micrograms/m$^2$.

6. Method of claim 5 wherein said clonidine is administered in an amount of about 150 micrograms/m$^2$.

7. Method of claim 1 wherein said peptide is GRF 1-44, GRF 1-40, GRF 1-37, or GRF 1-29.

8. Method of claim 7 wherein said peptide is administered in an amount of about 1 μg/kg i.v. or about 10 μg/kg s.c.

9. Method of claim 1 wherein said agonist is clonidine, said peptide is GRF 1-44, GRF 1-40, GRF 1-37, or GRF 1-29, and said clonidine is administered from 0 to about 120 minutes prior to said peptide.

10. Method of claim 9 wherein said clonidine is administered in an amount of from about 100 to about 300 micrograms/m$^2$, and said peptide is administered in an amount of about 1 μg/kg i.v. or about 10 μg/kg s.c.

11. Method of claim 9 wherein said peptide is GRF 1-29.

12. Method of providing for differential diagnosis and treatment of one of the various states of growth hormone insufficiency in a child of growth stature below the tenth percentile, which comprises in a standardizing procedure, cojointly administering an alpha-2-adrenergic agonist in an amount effective to inhibit somatostatin release by the hypothalamus and a growth hormone releasing peptide in an amount effective to stimulate growth hormone release, to a plurality of first children of normal growth stature, not exhibiting growth hormone insufficiency, and of known chronological ages, bone ages and growth velocities, said peptide stimulating a growth hormone response consequent said administering of said agonist, ascertaining by assay the elicited amounts of growth hormone release, and correlating the ascertained elicited amounts with the known chronological ages, bone ages and growth velocities of the first children to obtain a set of standard responder data including mean and standard deviation values of the growth hormone release elicited amounts and of the corresponding bone age to growth velocity ratios, for indicating the theoretical growth hormone release elicited amount corresponding to a child of known chronological age, bone age and growth velocity, in a test procedure, cojointly administering said agonist and peptide in said amounts, to a plurality of second children of growth stature below the tenth percentile, individually exhibiting respectively one of the various states of growth hormone insufficiency, and of known chronological ages, bone ages and growth velocities, ascertaining by assay the elicited amounts of growth hormone release and thereby individually those above a predetermined amount constituting about 10 micrograms/L for defining a positive response and those below said predetermined amount for defining a negative response, and correlating the ascertained elicited amounts with the known chronological ages, bone ages and growth velocities of the second children to obtain a set of test responder data, in a diagnosing procedure, correlating said test data with said standard data, including correlating the test procedure growth hormone release elicited amounts with the standardizing procedure theoretical growth hormone release elicited amounts corresponding to the chronological ages, bone ages and growth velocities of the second children to provide a percentage deviation of the test procedure elicited amounts relative to the theoretical elicited amounts for defining a normal response as being within an about −20 to +20% deviation range and within the standard deviation value of the standard responder data growth hormone release elicited amounts, a low response as being below said deviation range and a high response as being above said deviation range, and correlating the percentage deviation defined responses with the standard deviation values of the corresponding bone age to growth velocity ratios of the standard responder data, to form a corresponding chronological age, bone age and growth velocity based data system for differentially diagnosing the second children among the following groups of growth hormone responders to said test procedure:

(1) a low responder having low growth velocity for corresponding bone age, such that the responder having said positive response is diagnosed as having neurosecretory dysfunction and the responder having said negative response is diagnosed as having pituitary dysfunction, (2) a low responder having normal growth velocity for corresponding bone age is diagnosed as having constitutional growth delay, (3) a normal responder having low growth velocity for corresponding bone age is diagnosed as having pre-pubertal familial short stature, (4) a normal responder having normal growth velocity for corresponding bone age is diagnosed as having post-pubertal familial short stature, and (5) a high responder having low growth velocity for corresponding bone age is diagnosed as malnourished, wherein a normal responder is defined as having a said growth hormone release within said about −20 to +20% deviation range, a low responder is defined as having a said growth hormone release lower than that of a normal responder, and a high responder is defined as having a said growth hormone release higher than that of a normal responder, and on the basis of said data system, for differentially diagnosing a child of growth stature below the tenth percentile and of known chronological age, bone age and growth velocity, and suspected of having a growth hormone deficiency, cojointly administering to the child said agonist and peptide in said amounts, and ascertaining by assay the elicited amount of growth hormone release and thereby whether the elicited amount is above said predetermined amount for defining a positive response or below said predetermined amount for defining a negative response, whereby to indicate on the basis of the ascertained elicited amount and said positive or negative response and the known chronological age, bone age and growth velocity of the child, by way of differential diagnosis, whether the child corresponds to one of the aforesaid groups (1) to (5) of growth hormone responders to such cojoint administration, and in dependence upon the indication of whether the child corresponds to one of the aforesaid groups (1) to (5) of growth hormone responders to such cojoint administration, chronically administering to the child an effective amount of growth hormone upon an indicated diagnosis of group (1) and a said negative response, or chronically cojointly administering to the child said agonist and peptide in said amounts upon an indicated diagnosis of group (1) and a said positive response, or of group (2) or group (3) or group (4).

13. Method of claim 12 wherein said growth stature below the tenth percentile is below the third percentile.

14. Method of claim 12 wherein said agonist is clonidine.

15. Method of claim 12 wherein said clonidine is administered from 0 to about 120 minutes prior to said peptide.

16. Method of claim 12 wherein said peptide is GRF 1-44, GRF 1-40, GRF 1-37, or GRF 1-29.

17. Method of claim 12 wherein said agonist is clonidine, said peptide is GRF 1-44, GRF 1-40, GRF 1-37, or GRF 1-29, and said clonidine is administered from 0 to about 120 minutes prior to said peptide.

18. Method of differentially diagnosing a child of growth stature below the tenth percentile and of known chronological age, bone age and growth velocity, and suspected of having a growth hormone insufficiency, and of treating a child so diagnosed, which comprises cojointly administering to the child an alpha-2-adrenergic agonist in an amount effective to inhibit somatostatin release by the hypothalamus and a growth hormone releasing peptide in an amount effective to stimulate growth hormone release, said peptide stimulating a growth hormone response consequent said administering of said agonist, and ascertaining by assay the elicited amount of growth hormone release and thereby whether the elicited amount is above a predetermined amount constituting about 10 micrograms/L for defining a positive response or below said predetermined amount for defining a negative response, whereby to indicate on the basis of the ascertained elicited amount and said positive or negative response and the known chronological age, bone age and growth velocity, by way of differential diagnosis, whether the child corresponds to one of the following groups of growth hormone responders to such cojoint administration:

(1) a low responder having low growth velocity for corresponding bone age, such that the responder having said positive response is diagnosed as having neurosecretory dysfunction and the responder having said negative response is diagnosed as having pituitary dysfunction, (2) a low responder having normal growth velocity for corresponding bone age is diagnosed as having constitutional growth delay, (3) a normal responder having low growth velocity for corresponding bone age is diagnosed as having pre-pubertal familial short stature, (4) a normal responder having normal growth velocity for corresponding bone age is diagnosed as having post-pubertal familial short stature, and (5) a high responder having low growth velocity for corresponding bone age is diagnosed as malnourished, said differential diagnosis being based on the following steps:

in a standardizing procedure, cojointly administering an alpha-2-adrenergic agonist in an amount effective to inhibit somatostatin release by the hypothalamus and a growth hormone releasing peptide in an amount effective to stimulate growth hormone release, to a plurality of first children of normal growth stature, not exhibiting growth hormone insufficiency, and of known chronological ages, bone ages and growth velocities, said peptide stimulating a growth hormone response consequent said administering of said agonist, ascertaining by assay the elicited amounts of growth hormone release, and correlating the ascertained elicited amounts with the known chronological ages, bone ages and growth velocities of the first children to obtain a set of standard responder data including mean and standard deviation values of the growth hormone release elicited amounts and of the corresponding bone age to growth velocity ratios, for indicating the theoretical growth hormone release elicited amount corresponding to a child of known chronological age, bone age and growth velocity, in a test procedure, cojointly administering said agonist and peptide in said amounts, to a plurality of second children of growth stature below the tenth percentile, individually exhibiting respectively one of the various states of growth hormone insufficiency, and of known chronological ages, bone ages and growth velocities, ascertaining by the elicited amounts of growth hormone release and thereby individually those above a predetermined amount constituting about 10 micrograms/L for defining a positive response and those below said predetermined amount for defining a negative response, and correlating the ascertained elicited amounts with the known chronological ages, bone ages and growth velocities of the second children to obtain a set of test responder data, and in a diagnosing procedure, correlating said test data with said standard data, including correlating the test procedure growth hormone release elicited amounts with the standardizing procedure theoretical growth hormone release elicited amounts corresponding to the chronological ages, bone ages and growth velocities of the second children to provide a percentage deviation of the test procedure elicited amounts relative to the theoretical elicited amounts for defining a normal response as being within an about $-20$ to $+20\%$ deviation range and within the standard deviation value of the standard responder data growth hormone release elicited amounts, a low response as being below said deviation range and a high response as being above said deviation range, and correlating the percentage deviation defined responses with the standard deviation values of the corresponding bone age to growth velocity ratios of the standard responder data, to form a corresponding chronological age, bone age and growth velocity based data system for differentially diagnosing the second children among the aforesaid groups (1) to (5), wherein a normal responder is defined as having a said growth hormone release within said about $-20$ to $+20\%$ deviation range, a low responder is defined as having a said growth hormone release lower than that of a normal responder, and a high responder is defined as having a said growth hormone release higher than that of a normal responder, and in dependence upon the indication of whether the child corresponds to one of the aforesaid groups (1) to (5) of growth hormone responders to such cojoint administration, chronically administering to the child an effective amount of growth hormone upon an indicated diagnosis of group (1) and a said negative response, or chronically cojointly administering to the child said agonist and peptide in said amounts upon an indicated diagnosis of group (1) and a said positive response.

19. Method of claim 18 wherein said growth stature below the tenth percentile is below the third percentile.

* * * * *

UNITED STATES PATENT AND TRADEMARK OFFICE
CERTIFICATE OF CORRECTION

PATENT NO. : 5,428,013
DATED : June 27, 1995
INVENTOR(S) : Jesus Devesa Mugica It is certified that error appears in the above-identified patent and that said Letters Patent is hereby corrected as shown below:

On the title page of the Letters Patent, please correct the inventor data as follows:

[76] Inventor: Jesus Devesa Mugica, Chalet "As Gaivotas" Lamas Cacheira, 15883 Teo (La Cornua), Spain Signed and Sealed this Nineteenth Day of September, 1995

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,428,013
DATED : June 27, 1995
INVENTOR(S) : Jesus Devesa Mugica It is certified that error appears in the above-identified patent and that said Letters Patent is hereby corrected as shown below:

On the Title page, item [56], please add:

Attorney/Agent/Firm: McGlew and Tuttle, P.C.

Signed and Sealed this

Tenth Day of October, 1995

*Attest:*

BRUCE LEHMAN

*Attesting Officer*     *Commissioner of Patents and Trademarks*